US00PP29664P2

(12) United States Plant Patent
Boldt

(10) Patent No.: US PP29,664 P2
(45) Date of Patent: Sep. 11, 2018

(54) *PETUNIA* PLANT NAMED 'USTUN2401M'

(50) Latin Name: *Petunia X hybrida*
Varietal Denomination: USTUN2401M

(71) Applicant: Jessica Boldt, Allenstown, NH (US)

(72) Inventor: Jessica Boldt, Allenstown, NH (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/731,455

(22) Filed: Jun. 12, 2017

(51) Int. Cl.
*A01H 5/02* (2018.01)

(52) U.S. Cl.
USPC ..... Plt./356.21
CPC ..... *A01H 5/0277* (2013.01)

(58) Field of Classification Search
USPC ..... Plt./356.21, 356.13, 356.1
CPC ..... A01H 5/0277
See application file for complete search history.

(56) References Cited

PUBLICATIONS

CA PBR Citation for 'USTUN2401M' as per CA PBR 17-9132; Apr. 28, 2017; 1 page.*

* cited by examiner

*Primary Examiner* — Kent L Bell
(74) *Attorney, Agent, or Firm* — C. A. Whealy

(57) ABSTRACT

A new and distinct *Petunia* plant named 'USTUN2401M', characterized by its compact, outwardly spreading and mounding to eventually trailing plant habit; freely branching habit; vigorous growth habit; early and freely flowering habit; hot pink-colored flowers; and good garden performance.

1 Drawing Sheet

Botanical designation: *Petunia* X *hybrida.*
Cultivar denomination: 'USTUN2401M'.

BACKGROUND OF THE INVENTION

The present invention relates to a new and distinct cultivar of *Petunia* plant, botanically known as *Petunia* X *hybrida* and hereinafter referred to by the name 'USTUN2401M'.

The new *Petunia* plant is a naturally-occurring branch mutation of *Petunia* X *hybrida* 'USTUNJ2401', disclosed in U.S. Plant Pat. No. 28,028. The new *Petunia* plant was discovered and selected by the Inventor on a single flowering plant within a population of plants of 'USTUNJ2401' in a controlled greenhouse environment in Loudon, N.H. in early January, 2015.

Asexual reproduction of the new *Petunia* plant by vegetative terminal cuttings in a controlled greenhouse environment in Loudon, N.H. since January, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN2401M'. These characteristics in combination distinguish 'USTUN2401M' as a new and distinct *Petunia* plant:

1. Compact, outwardly spreading and mounding to eventually trailing plant habit.
2. Freely branching habit.
3. Vigorous growth habit.
4. Early and freely flowering habit.
5. Hot pink-colored flowers.
6. Good garden performance.

Plants of the new *Petunia* can be compared to plants of the mutation parent, 'USTUNJ2401'. In side-by-side comparisons, plants of the new *Petunia* differ primarily from plants of 'USTUNJ2401' in flower color as plants of 'USTUNJ2401' have white-colored flowers with a distinct and stable red purple star-shaped color pattern.

Plants of the new *Petunia* can be compared to plants of 'USTUN34803', disclosed in U.S. Plant Pat. No. 22,884. In side-by-side comparisons, plants of the new *Petunia* differ primarily from plants of 'USTUN34803' in the following characteristics:

1. Plants of the new *Petunia* are more mounding than plants of 'USTUN34803'.
2. Plants of the new *Petunia* and 'USTUN34803' differ in flower color as plants of 'USTUN34803' have red purple-colored flowers.

Plants of the new *Petunia* can also be compared to plants of 'USTUN19603', disclosed in U.S. Plant Pat. No. 21,675. In side-by-side comparisons, plants of the new *Petunia* differ primarily from plants of 'USTUN19603' in the following characteristics:

1. Plants of the new *Petunia* are more mounding than plants of 'USTUN19603'.
2. Plants of the new *Petunia* flower earlier than plants of 'USTUN19603'.

3. Flowers of plants of the new *Petunia* are darker pink than flowers of plants of 'USTUN19603'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'USTUN2401M' grown in a container.

The photograph at the top of the sheet is a close-up view of a typical flowering plant of 'USTUN2401M'.

DETAILED BOTANICAL DESCRIPTION

The aforementioned photographs and following observations and measurements describe plants grown during the early spring in 11.5-cm containers in an acrylic-covered greenhouse in Carleton, Mich. and under cultural practices typical of commercial *Petunia* production. During the production of the plants, day and night temperatures ranged from 18° C. to 27° C. Plants were seven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'USTUN2401M'.

Parentage: Naturally-occurring branch mutation of *Petunia* X *hybrida* 'USTUNJ2401', disclosed in U.S. Plant Pat. No. 28,028.

Propagation:

*Type*.—Terminal vegetative cuttings.

*Time to initiate roots, summer*.—About three to four days at temperatures ranging from 17° C. to 29° C.

*Time to initiate roots, winter*.—About five to seven days at temperatures ranging from 17° C. to 21° C.

*Time to produce a rooted plant, summer*.—About three weeks at temperatures ranging from 17° C. to 29° C.

*Time to produce a rooted plant, winter*.—About four weeks at temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, outwardly spreading and mounding to eventually trailing plant habit; freely branching habit with about seven to eight primary lateral branches with three to four secondary lateral branches per primary lateral branch developing; dense and bushy appearance; pinching enhances development of lateral branches; vigorous growth habit.

*Plant height, soil level to top of foliar plane*.—About 9.5 cm.

*Plant height, soil level to top of floral plane*.—About 12 cm.

*Plant diameter* (*area of spread*).—About 29 cm.

*Lateral branches*.—Length: About 16 cm. Diameter: About 3 mm. Internode length: About 1 cm to 1.5 cm. Strength: Strong. Aspect: Initially upright then outwardly spreading. Texture and luster: Minute pubescence; matte. Color, developing: Close to 144B. Color, developed: Close to 144A.

Leaf description:

*Arrangement*.—Alternate before flowering; opposite after flowers develop; leaves simple.

*Length*.—About 3.6 cm.

*Width*.—About 1.8 cm.

*Shape*.—Elliptical.

*Apex*.—Broadly acute.

*Base*.—Attenuate.

*Margin*.—Entire.

*Texture and luster, upper and lower surfaces*.—Sparsely pubescent; matte.

*Venation pattern*.—Pinnate, arcuate.

*Color*.—Developing leaves, upper and lower surfaces: Close to 146B. Fully expanded leaves, upper surface: Close to 147A; venation, close to 147B. Fully expanded leaves, lower surface: Close to 147B; venation, close to 147C to 147D.

*Petioles*.—Length: About 8 mm. Diameter: About 2 mm. Strength: Moderately strong. Texture and luster, upper and lower surfaces: Sparsely pubescent; matte. Color, upper surface: Close to 146C. Color, lower surface: Close to 146D.

Flower description:

*Flower type and flowering habit*.—Single axillary salverform flowers; flowers face mostly upward to outwardly; freely flowering habit with about more than 100 flowers developing per plant during the flowering season.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About four to five days; flowers persistent.

*Fragrance*.—None detected.

*Flower buds*.—Length: About 2.7 cm. Diameter: About 5 mm. Shape: Oblong, elongate. Texture and luster: Pubescent; matte. Color: Close to 186C.

*Flower diameter*.—About 3.6 cm by 3.4 cm.

*Flower depth* (*height*).—About 3.4 cm.

*Throat diameter, distal*.—About 9 mm.

*Tube length*.—About 2.7 cm.

*Tube diameter*.—About 7 mm.

*Petals*.—Quantity and arrangement: Five petals fused in a single salverform whorl. Petal lobe length (from throat): About 1.6 cm. Petal lobe width: About 2 cm. Petal lobe shape: Fan-shaped. Petal lobe apex: Broadly acute. Petal lobe margin: Entire, undulate. Petal lobe texture and luster, upper surface: Smooth, glabrous; velvety; matte. Petal lobe texture and luster, lower surface: Sparsely pubescent; matte. Throat texture: Smooth, glabrous. Tube texture: Minute pubescence. Color: When opening, upper surface: Close to 71C. When opening, lower surface: Close to 186C. Fully opened, upper surface: Close to 71C; venation, close to 71A; color becoming closer to 71D with development. Fully opened, lower surface:

Close to 75B; venation, close to 195A; color becoming closer to 76C with development. Flower throat (inside): Close to N77B tinted with close to 64B; venation, close to 64A. Flower tube (outside): Close to N77B; venation, close to 195A.

*Sepals*.—Quantity and arrangement: Five sepals fused in a single star-shaped whorl. Calyx length: About 1.4 cm. Calyx diameter: About 1.3 cm. Length: About 1 cm. Width: About 2 mm. Shape: Lanceolate. Apex: Rounded. Margin: Entire. Texture and luster, upper and lower surfaces: Minute pubescence; minute; matte. Color: When developing, upper and lower surfaces: Close to 146B. Fully developed, upper and lower surfaces: Close to 146B.

*Peduncles*.—Length: About 2.1 cm. Width: About 1.5 mm. Strength: Moderately strong. Angle: About 45° from the stem axis. Texture and luster: Pubescent; matte. Color: Close to 146C.

*Reproductive organs*.—Stamens: Quantity per flower: Five. Filament length: About 9 mm. Filament color: Close to 145D. Anther length: About 1 mm. Anther shape: Round. Anther color: Close to 201C. Pollen amount: Scarce. Pollen color: Close to 97B. Pistils: Quantity per flower: One. Pistil length: About 1.7 cm. Style length: About 1.2 cm. Style color: Close to 145D. Stigma diameter: About 1.5 mm. Stigma shape: Round. Stigma color: Close to 146A. Ovary color: Close to 145B.

*Seeds and fruits*.—Seed and fruit development has not been observed on plants of the new *Petunia* to date.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN2401M' as illustrated and described.

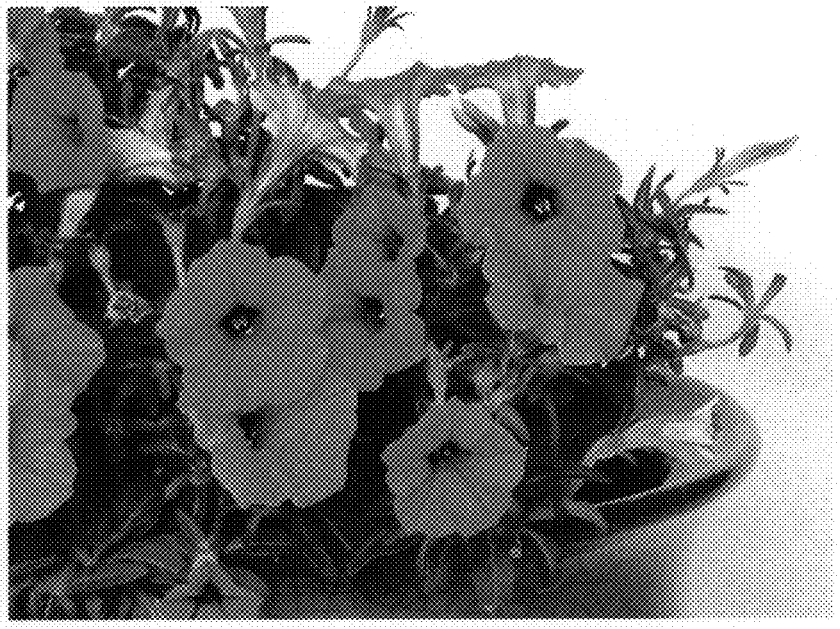
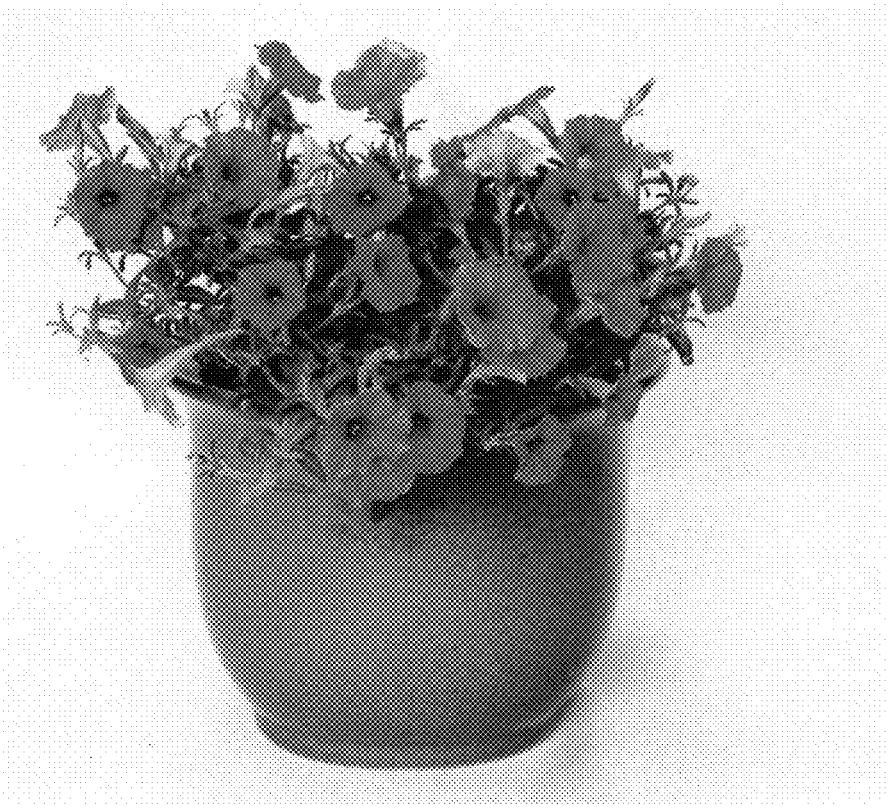

* * * * *